(12) United States Patent
Bilyeu et al.

(10) Patent No.: US 8,728,726 B1
(45) Date of Patent: May 20, 2014

(54) RS2 MUTANT ALLELE, PERFECT MOLECULAR MARKERS, AND LOW RAFFINOSE/STACHYOSE SOYBEAN GERMPLASM

(75) Inventors: Kristin D. Bilyeu, Columbia, MO (US); Emily C. Dierking, Lafayette, IN (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 217 days.

(21) Appl. No.: 13/176,910

(22) Filed: Jul. 6, 2011

Related U.S. Application Data

(60) Provisional application No. 61/362,738, filed on Jul. 9, 2010.

(51) Int. Cl.
*A01H 5/00* (2006.01)
*C12Q 1/68* (2006.01)
*A01H 1/04* (2006.01)

(52) U.S. Cl.
USPC .......................... 435/6.1; 800/312; 800/266

(58) Field of Classification Search
None
See application file for complete search history.

(56) References Cited

U.S. PATENT DOCUMENTS

| 5,710,365 | A | | 1/1998 | Kerr | |
| 6,147,193 | A | * | 11/2000 | Kerr et al. | 530/378 |
| 6,337,430 | B1 | * | 1/2002 | Ishige et al. | 800/278 |
| 7,723,567 | B1 | * | 5/2010 | Watanabe et al. | 800/284 |

OTHER PUBLICATIONS

Li et al, 2007, Biotechnol. Lett., 29:635-640.*
Dierking et al, 2008, The Plant Genome, 1:135-145.*
Dierking, Emily C., et al, "New sources of soybean seed meal and oil composition traits identified through TILLING", BioMed Central, BMC Plant Biology, Published Jul. 13, 2009, available from http://www.biomedcentral.com/1471-2229/9/89.

\* cited by examiner

*Primary Examiner* — Ashwin Mehta
*Assistant Examiner* — Jason Deveau Rosen
(74) *Attorney, Agent, or Firm* — Elizabeth R. Sampson; John Fado; Lesley Shaw

(57) ABSTRACT

A mutation in the gene encoding the raffinose synthase 2 enzyme, RS2, in soybean, *Glycine max* (L.) Merr., is associated with a reduced raffinose and stachyose seed phenotype. Soybean homozygous for a mutant allele of the RS2 gene which encodes an amino acid change to isoleucine at position 107 of the enzyme's amino acid sequence exhibit significantly reduced seed raffinose and stachyose content, and increased seed sucrose content. Nucleic acid samples of soybean may be assayed for the presence of this mutant allele, and soybean containing the allele may be selected for breeding to generate reduced raffinose and stachyose soybean lines. Alternatively, the mutation may be detected by analysis of the RS2 enzyme produced in the soybean to determine the presence of either an isoleucine or a threonine at amino acid 107. Molecular markers have been developed for detecting the presence or absence of the mutant allele.

19 Claims, 4 Drawing Sheets

```
atggctccaagcataagcaaaactgtggaactaaattcatttggtct
tgtcaacggtaatttgcctttgtccataacccagaaggatcaaatttcc
tcgccaacggccacccttttctcacggaagttcccgaaaacataatagtc
acccctcacccatcgacgccaagagtagtaagaacaacgaggacgacga
cgtcgtaggttgcttcgtgggcttccacgcggacgagcccagaagccgac
acgtggcttccctggggaagctcagaggaataaaattcatgagcatattc
cggtttaaggtgtggtggaccactcactgggtcggtagcaacggacacga
actggagcacgagacacagatgatgcttctcgacaaaaacgaccagctcg
gacgcccctttgtgttgattctcccgatcctccaagcctcgttccgagcc
tccctgcaacccggtttggatgattacgtggacgtttgcatggagagcgg
gtcgacacgtgtctgtggctccagcttcgggagctgcttatacgtccacg
ttggccatgacccgtatcagttgcttagagaagcaactaaagtcgttagg
atgcatttggggacgttcaagcttctcgaggagaaaaccgcgccagtgat
catagacaagtttggttggtgtacatgggacgcgttttacttgaaggtgc
atccctcaggtgtgtgggaaggggtgaaagggttggtggagggagggtgc
cctccagggatggtcctaatcgacgacgggtggcaagccatttgtcacga
cgaggaccccataacggaccaagagggtatgaagcgaacctccgcagggg
agcaaatgccatgcaggttggtgaagttggaggaaaattacaagttcaga
cagtattgtagtggaaaggattctgagaagggtatgggtgcctttgttag
ggacttgaaggaacagtttaggagcgtggagcaggtgtatgtgtggcacg
cgctttgtgggtattggggtggggtcagacccaaggttccgggcatgccc
caggctaaggttgtcactccgaagctgtccaatggactaaaattgacaat
gaaggatttagcggtggataagatcgtcagtaacggagttggactggtgc
caccacacctggctcaccttttgtacgaagggctccactccgtttggaa
tctgcgggtattgacggtgttaaggttgacgttatacacttgctcgagat
gctatccgaggaatacggtggccgtgttgagctagccaaagcttattaca
aagcgctcactgcttcggtgaagaagcatttcaaaggcaatggggtcatt
gcgagcatggagcattgtaatgacttctttctccttggtaccgaagccat
agcccttgggcgcgtaggagatgattttggtgcactgatccctctggag
atccaaatggcacgtattggctccaagggtgtcacatggtgcactgtgcc
tacaacagcttgtggatggggaattttattcagccggattgggacatgtt
ccagtccactcacccttgtgccgaattccatgcagcctctagggccatct
ctggtggaccagtttacgttagtgattgtgttggaaagcacaacttcaag
ttgctcaagagcctcgctttgcctgatgggacgattttgcgttgtcaaca
ctatgcactccccacacgagactgtttgtttgaagaccccttgcatgatg
ggaagacaatgctcaaaatttggaatctcaacaaatatacaggtgttttg
ggtctatttaattgccaaggaggtgggtggtgtcccgtaactaggagaaa
caagagtgcctctgaattttcacaaactgtgacatgcttagcgagtcctc
aagacattgaatggagcaatgggaaaagcccaatatgcataaaagggatg
aatgtgtttgctgtatatttgttcaaggaccacaaactaaagctcatgaa
ggcatcagagaaattggaagtttcacttgagccatttacttttgagctat
tgacagtgtctccagtgattgtgctgtcaaaaaagttaattcaatttgct
ccaattggattagtgaacatgcttaacactggtggtgccattcagtccat
ggagtttgacaaccacatagatgtggtcaaaattggggttaggggttgtg
gggagatgaaggtgtttgcatcagagaaaccagttagttgcaaactagat
ggggtagttgtaaaatttgattatgaggataaaatgctgagagtgcaagt
tccctggcctagtgcttcaaaattgtcaatggttgagttttatttga
```

FIG. 1

```
MAPSISKTVELNSFGLVNGNLPLSITLEGSNFLANGHPFLTEVPENIIVT
PSPIDAKSSKNNEDDDVVGCFVGFHADEPRSRHVASLGKLRGIKFMSIFR
FKVWWTTHWVGSNGHELEHETQMMLLDKNDQLGRPFVLILPILQASFRAS
LQPGLDDYVDVCMESGSTRVCGSSFGSCLYVHVGHDPYQLLREATKVVRM
HLGTFKLLEEKTAPVIIDKFGWCTWDAFYLKVHPSGVWEGVKGLVEGGCP
PGMVLIDDGWQAICHDEDPITDQEGMKRTSAGEQMPCRLVKLEENYKFRQ
YCSGKDSEKGMGAFVRDLKEQFRSVEQVYVWHALCGYWGGVRPKVPGMPQ
AKVVTPKLSNGLKLTMKDLAVDKIVSNGVGLVPPHLAHLLYEGLHSRLES
AGIDGVKVDVIHLLEMLSEEYGGRVELAKAYYKALTASVKKHFKGNGVIA
SMEHCNDFFLLGTEAIALGRVGDDFWCTDPSGDPNGTYWLQGCHMVHCAY
NSLWMGNFIQPDWDMFQSTHPCAEFHAASRAISGGPVYVSDCVGKHNFKL
LKSLALPDGTILRCQHYALPTRDCLFEDPLHDGKTMLKIWNLNKYTGVLG
LFNCQGGGWCPVTRRNKSASEFSQTVTCLASPQDIEWSNGKSPICIKGMN
VFAVYLFKDHKLKLMKASEKLEVSLEPFTFELLTVSPVIVLSKKLIQFAP
IGLVNMLNTGGAIQSMEFDNHIDVVKIGVRGCGEMKVFASEKPVSCKLDG
VVVKFDYEDKMLRVQVPWPSASKLSMVEFLF*
```

FIG. 2

```
atggctccaagcataagcaaaactgtggaactaaattcatttggtcttgt
caacggtaatttgcctttgtccataaccctagaaggatcaaatttcctcg
ccaacggccacccttttctcacggaagttcccgaaaacataatagtcacc
ccttcacccatcgacgccaagagtagtaagaacaacgaggacgacgacgt
cgtaggttgcttcgtgggcttccacgcggacgagcccagaagccgacacg
tggcttccctggggaagctcagaggaataaaattcatgagcatattccgg
tttaaggtgtggtggaccaTtcactgggtcggtagcaacggacacgaact
ggagcacgagacacagatgatgcttctcgacaaaaacgaccagctcggac
gcccctttgtgttgattctcccgatcctccaagcctcgttccgagcctcc
ctgcaacccggtttggatgattacgtggacgtttgcatggagagcggtc
gacacgtgtctgtggctccagcttcgggagctgcttatacgtccacgttg
gccatgacccgtatcagttgcttagagaagcaactaaagtcgttaggatg
catttggggacgttcaagcttctcgaggagaaaaccgcgccagtgatcat
agacaagtttggttggtgtacatgggacgcgttttacttgaaggtgcatc
cctcaggtgtgtgggaaggggtgaagggttggtggagggagggtgccct
ccagggatggtcctaatcgacgacggtggcaagccatttgtcacgacga
ggaccccataacggaccaagagggtatgaagcgaacctccgcaggggagc
aaatgccatgcaggttggtgaagttggaggaaaattacaagttcagacag
tattgtagtggaaaggattctgagaagggtatgggtgcctttgttaggga
cttgaaggaacagtttaggagcgtggagcaggtgtatgtgtggcacgcgc
tttgtgggtattgggtgggtcagacccaaggttccgggcatgccccag
gctaaggttgtcactccgaagctgtccaatggactaaaattgacaatgaa
ggatttagcggtggataagatcgtcagtaacggagttggactggtgccac
cacacctggctcacctttgtacgaagggctccactcccgtttggaatct
gcgggtattgacggtgttaaggttgacgttatacacttgctcgagatgct
atccgaggaatacggtggccgtgttgagctagccaaagcttattacaaag
cgctcactgcttcggtgaagaagcatttcaaaggcaatggggtcattgcg
agcatggagcattgtaatgacttctttctccttggtaccgaagccatagc
ccttgggcgcgtaggagatgattttggtgcactgatccctctggagatc
caaatggcacgtattggctccaagggtgtcacatggtgcactgtgcctac
aacagcttgtggatggggaattttattcagccggattgggacatgttcca
gtccactcaccttgtgccgaattccatgcagcctctagggccatctctg
gtggaccagtttacgttagtgattgtgttggaaagcacaacttcaagttg
ctcaagagcctcgctttgcctgatgggacgattttgcgttgtcaacacta
tgcactccccacacgagactgtttgtttgaagacccccttgcatgatggga
agacaatgctcaaaatttggaatctcaacaaatatacaggtgttttgggt
ctatttaattgccaaggaggtgggtggtgtcccgtaactaggagaaacaa
gagtgcctctgaattttcacaaactgtgacatgcttagcgagtcctcaag
acattgaatggagcaatgggaaaagcccatatgcataaaagggatgaat
gtgtttgctgtatatttgttcaaggaccacaaactaaagctcatgaaggc
atcagagaaattggaagtttcacttgagccatttacttttgagctattga
cagtgtctccagtgattgtgctgtcaaaaagttaattcaatttgctcca
attggattagtgaacatgcttaacactggtggtgccattcagtccatgga
gtttgacaaccacatagatgtggtcaaaattggggttaggggttgtgggg
agatgaaggtgtttgcatcagagaaaccagttagttgcaaactagatggg
gtagttgtaaaatttgattatgaggataaaatgctgagagtgcaagttcc
ctggcctagtgcttcaaaattgtcaatggttgagttttattttga
```

FIG. 3

MAPSISKTVELNSFGLVNGNLPLSITLEGSNFLANGHPFLTEVPENIIVT
PSPIDAKSSKNNEDDDVVGCFVGFHADEPRSRHVASLGKLRGIKFMSIFR
FKVWWTIHWVGSNGHELEHETQMMLLDKNDQLGRPFVLILPILQASFRAS
LQPGLDDYVDVCMESGSTRVCGSSFGSCLYVHVGHDPYQLLREATKVVRM
HLGTFKLLEEKTAPVIIDKFGWCTWDAFYLKVHPSGVWEGVKGLVEGGCP
PGMVLIDDGWQAICHDEDPITDQEGMKRTSAGEQMPCRLVKLEENYKFRQ
YCSGKDSEKGMGAFVRDLKEQFRSVEQVYVWHALCGYWGGVRPKVPGMPQ
AKVVTPKLSNGLKLTMKDLAVDKIVSNGVGLVPPHLAHLLYEGLHSRLES
AGIDGVKVDVIHLLEMLSEEYGGRVELAKAYYKALTASVKKHFKGNGVIA
SMEHCNDFFLLGTEAIALGRVGDDFWCTDPSGDPNGTYWLQGCHMVHCAY
NSLWMGNFIQPDWDMFQSTHPCAEFHAASRAISGGPVYVSDCVGKHNFKL
LKSLALPDGTILRCQHYALPTRDCLFEDPLHDGKTMLKIWNLNKYTGVLG
LFNCQGGGWCPVTRRNKSASEFSQTVTCLASPQDIEWSNGKSPICIKGMN
VFAVYLFKDHKLKLMKASEKLEVSLEPFTFELLTVSPVIVLSKKLIQFAP
IGLVNMLNTGGAIQSMEFDNHIDVVKIGVRGCGEMKVFASEKPVSCKLDG
VVVKFDYEDKMLRVQVPWPSASKLSMVEFLF\*

FIG. 4

SEQUENCE LISTING

```
<160> NUMBER OF SEQ ID NOS: 12

<210> SEQ ID NO 1
<211> LENGTH: 12935
<212> TYPE: DNA
<213> ORGANISM: Glycine max

<400> SEQUENCE: 1
tttttagtca gattatacaa ttctagctag tactttattt tttctatcac gtacatccaa      60
tatcattttt ttcatagcag ttcatgaaat attttattaa atattaatta aagcataatt     120
tgacctctaa ggtgtgacac gtgtaactaa tatagctttg attttttttt attatggttt     180
attttatatt caaaatctat cctgatttaa attctaaata atggattaaa aaacataaat     240
tactacacta attgagtcaa caattattac tgtcgtcggt tcaactttga gcttttaagt     300
atatgagagt ggttgaattg ctgcctatat gaataaaaca atatttatgg gggataaaaa     360
tgagtctcat attgtacatg gtagtttgac tttgacacat atacccttttg ctctggctgt     420 aactagaatg cactaggcac aattaaacaa aaataaattc tccttctcta tataaaccca     480
ccatgtcacc acaccctacc cagcaaaacc aaaccatagc aaacctaagc accaaacctc     540
tttctttcaa gatccttgaa ttcagtccca tggctccaag cataagcaaa actgtggaac     600
taaattcatt tggtcttgtc aacggtaatt tgcctttgtc cataacccta gaaggatcaa     660
atttcctcgc caacggccac ccttttctca cggaagttcc cgaaaacata atagtcaccc     720
cttcacccat cgacgccaag agtagtaaga acaacgagga cgacgacgtc gtaggttgct     780
tcgtgggctt ccacgcggac gagcccagaa gccgacacgt ggcttccctg gggaagctca     840
```

```
gaggaataaa attcatgagc atattccggt ttaaggtgtg gtggaccact cactgggtcg      900
gtagcaacgg acacgaactg gagcacgaga cacagatgat gcttctcgac aaaaacgacc      960
agctcggacg cccctttgtg ttgattctcc cgatcctcca agcctcgttc cgagcctccc     1020
tgcaacccgg tttggatgat tacgtggacg tttgcatgga gagcgggtcg acacgtgtct     1080
gtggctccag cttcgggagc tgcttatacg tccacgttgg ccatgacccg tatcagttgc     1140
ttagagaagc aactaaagtc gttaggatgc atttggggac gttcaagctt ctcgaggaga     1200
aaaccgcgcc aggtatatac tcgccgctaa aaattcatca ccaaaattac tactgttttg     1260
ttttgttgga gtttttttt tttttttttt atatatataa taaggaggta ttttaaactt     1320
ttattgaatc tctcaactat tttttcactc tcttttttt acttatattt gactcataag     1380
aagcatcgaa ttgctatcaa attatattca ggcctgcaag ctttgaggga gtgtgtttat     1440
gtcatataat agaaataggg tatataaata aaggagaatc ctaactttt ttggttgaca     1500
taaatttaaa tttaaatcct aaaacacgag taatttataa ttttaaggat taaatatgtt     1560
tttagttttt ttattttggt tgaatgttat tttagttttt cttttatact gtctaattta     1620
gttcataaag tttataaaaa aacgtctttt taattcctct ttacaactta aattttaaa     1680
aaatggtgca aaaattaggc agtaggtcta ggaactaaaa ataagattat ataaaaacta     1740
aaaacacaat attcactaat cttaatgaga ttttttttaa aaaaatagta aaatttatt     1800
ttgtaaactg atttatttta tattgtagtg atcatagaca agtttggttg gtgtacatgg     1860
gacgcgtttt acttgaaggt gcatccctca ggtgtgtggg aagggtgaa agggttggtg     1920
gagggagggt gccctccagg gatggtccta atcgacgacg ggtggcaagc catttgtcac     1980
gacgaggacc ccataacgga ccaagagggt atgaagcgaa cctccgcagg ggagcaaatg     2040
ccatgcaggt tggtgaagtt ggaggaaaat tacaagttca gacagtattg tagtggaaag     2100
gattctgaga agggtatggg tgcctttgtt agggacttga aggaacagtt taggagcgtg     2160
gagcaggtgt atgtgtggca cgcgctttgt gggtattggg gtggggtcag acccaaggtt     2220
ccgggcatgc cccaggctaa ggttgtcact ccgaagctgt ccaatggact aaaattgaca     2280
atgaaggatt tagcggtgga taagatcgtc agtaacggag ttggactggt gccaccacac     2340
ctggctcacc ttttgtacga agggctccac tcccgtttgg aatctgcggg tattgacggt     2400
gttaaggttg acgttataca cgtaagtctc tactctgcat ttttgttttc tttttgacag     2460
tattgtctaa ccttttaact taattattta gatgaaaatt actcattttg attttgattt     2520
taatatggtg tttataggct tcagcaaaaa aaaaaaaaat ttggtgttta tagattagta     2580
atacatatag ttatagatta tagatgcctg tggaagaatt taagaattaa ttgatgatca     2640
aattgactac agtttagtta ctacagacta cagagtacct tagccatgtt tatgttctct     2700
gtagtgtatg ttttttagttt ccaaggtaac atttttgaact aaatatcaga attacttcgt     2760
aagtttaatt tgttgtcttt ggctacattt attcttgttt tctagtttgc tacgatactt     2820
gtacacggca agccatattt acaaatattt gtatgtggtg cttaaaaatt tgaaaggcaa     2880
attattcagt gaagtgtgta aaccgaaagt gaatatttct ttattggtgt atattaaaaa     2940
aactaagaat ttttatagta ttgatgactt aaaaaattta gattaaaaaa ctaataaaaa     3000
ataatgttga tgaatttaaa aatgtaatta ttgtataatt cgtttcctag gttggagaga     3060
atattgctta agttatataa agtaaataat tagaccaaaa tttgtttgac acaagtaatt     3120
tgacacttgc acacttggga ggcttaatca agatttgagt ttcaattttc aatttgagta     3180
tagagtcata acgagagatg ctactttatt acaaaatgaa atgagttaac ccggtgggag     3240
```

```
agaaatgagt tggatctcaa ataaaatacc ctagatatct cttggttaca tcaaaagaat   3300
ttttctttaa ttgtgacata taatggtaag atctatttaa gtggtgtaaa aagaaaaaaa   3360
aagagttgct aagttaaaga tctctaatat ttaatataat aatatatacc aatagtttta   3420
aattagaaaa atgatatatg ccttattgtt tggtatataa aatcaaaagg aaaaaataaa   3480
aataaaagag ataaagtgaa agaaagatct aataattaat aaataataca atgtcttaaa   3540
aagatatata aaaaataata taaaaataaa tatattatat aagtatataa attattatta   3600
ctaggggaaa gagatccacg tcttttctaaa aagaacttct ttttttaaat aaaacacaaa   3660
atgaaaaagg aaaagaacga gagaaagttg aaacaaaaat ggaagtgtgc aaatgtgcaa   3720
ttaactttat aaaatgatat atagttaaag atgatttaat ttttttaaaa aaagtaaaaa   3780
ccaaaaactt cgcattgtct ttattattaa ttatagatta tttagattaa gaaaaataaa   3840
tacaaataca gttttctata tgttagtgaa ctttgttgta aaaggttaca tgttactaaa   3900
tacacactag atgctctcat tatgtaaata tttgcaataa actacatgtt ctcatagtga   3960
tattttcttt aatactctat ataatttgtt taaatttatt agaaattagt aattttaatg   4020
agaagaactc atcaaaatgg atgattttta ataaatttca ataaaaatgg ttaagaaaaa   4080
gagtaagtat tgttagcatt tcttattttg aaaatataat agacgttagg ttagcaacat   4140
cagcacgttc aatattcttt ctgtatttaa gtgttagtct aataggacca accatctgca   4200
tatatacact acggttgtca taattgcagg gttgaaactt gaaagccaaa ttctctcaac   4260
taaaaatgat ttatcatgag attgagaagt gtctcttccc ttggcacttg tatccttcgt   4320
aggaccgcat caagtgagta tacgaggatc ttgctaaatt aatattacaa ctcacaagta   4380
tcaacgaggt ttccaacttc gtttgatact tggaggtatc attttactat aaaaaaatgc   4440
catttactaa taatttaatg ttgggtttga gaatcaagtt ggatcataat cagctatgaa   4500
gcccaagact ctataaagct agttctacat attaattggc ctcaagtggt ggctatacac   4560
aacggatttt tcaatatttc tattattata gcaaaacact aaactaaaca tagatcttga   4620
ttaaccatga ttacttagat gattttcaag tttaatattt cgtgatttgc attttttgcag   4680 ttgctcgaga tgctatccga ggaatacggt ggccgtgttg agctagccaa agcttattac   4740
aaagcgctca ctgcttcggt gaagaagcat ttcaaaggca atgggggtcat tgcgagcatg   4800 gagcattgta atgacttctt tctccttggt accgaagcca tagcccttgg gcgcgtaggt   4860
aataatcatt ccaaattgca gcccttataa taaacaataa cattagtagt caaagtattt   4920
taacttgatt ggttgaatat tatctctgag ttattgtaaa ttttgtaaat ttttttaatag   4980 tgtctttaat tctcacggaa aaaaatatat taatagatct ttccaaaaca tcaaaacttt   5040
aacatacaca aattttttgg agtttaatta tcatgtgtct tacacctaat taatcaaaaa   5100
tcatgtttga cataactttt aaaaaatttg tattaaaagt caataaatac gatagtttga   5160
gattgaacac aaagtaaaat tagtgtcaat gcattgtcta ttttctgaat tctccatcaa   5220
attttctaac ccataacaat acataaattc aggagatgat ttttggtgca ctgatccctc   5280
tggagatcca aatggcacgt attggctcca agggtgtcac atggtgcact gtgcctacaa   5340
cagcttgtgg atggggaatt ttattcagcc ggattgggac atgttccagt ccactcaccc   5400
ttgtgccgaa ttccatgcag cctctagggc catctctggt ggaccagttt acgttagtga   5460
ttgtgttgga aagcacaact tcaagttgct caagagcctc gctttgcctg atgggacgat   5520
tttgcgttgt caacactatg cactcccac acgagactgt tgtttgaag acccccttgca   5580 tgatgggaag acaatgctca aaatttggaa tctcaacaaa gtaagctacc ctctttttta   5640
```

```
aattattttt ttctttaatc cggtaaattt tttgtcagtg ttagggacta atcatctgag    5700
atgaaaaaaa acaattcaag aggtcggctg ggaattaaac ttttgatcac atatttaaga    5760
agaaattctt acatgatcta gactttaaac taccatgatt gcaaacaatc tttgtcccta    5820
ttgattattt ttttaattgg caaatgttag ttttgttaga aatgtcagtt tggaagattt    5880
gatatccttt catttttcct tcttctttca tctttcttc accactgaac caacctcgta     5940
tctttacatc ttattaaatt ttattttatt tttaatcgac aaatgttaat tattattatt    6000
gaattttatt aattgttttg agtgaaaatt agttgaaacc atgaaaaaat agtgatcatg    6060
caacttctaa tattttttt catgttatga agcatgctta tttgtcaatt atatcagatc     6120
aattaatttt ttaatcacac cataatgaca ttggaattat taataacctt tttatatttg    6180
tttttagtca gattatacaa ttctagctag tactttattt tttctatcac gtacatccaa    6240
tatcattttt ttcatagcag ttcatgaaat attttattaa atattaatta aagcataatt    6300
tgacctctaa ggtgtgacac gtgtaactaa tatagctttg attttttttt attatggttt    6360
attttatatt caaaatctat cctgatttaa attctaaata atggattaaa aaacataaat    6420
tactacacta attgagtcaa caattattac tgtcgtcggt tcaactttga gcttttaagt    6480
atatgagagt ggttgaattg ctgcctatat gaataaaaca atatttatgg gggataaaaa    6540
tgagtctcat attgtacatg gtagtttgac tttgacacat ataccctttg ctctggctgt    6600
aactagaatg cactaggcac aattaaacaa aaataaattc tccttctcta tataaaccca    6660
ccatgtcacc acaccctacc cagcaaaacc aaaccatagc aaacctaagc accaaacctc    6720 tttcttttcaa gatccttgaa ttcagtccca tggctccaag cataagcaaa actgtggaac    6780
taaattcatt tggtcttgtc aacggtaatt tgcctttgtc cataacccta gaaggatcaa    6840
atttcctcgc caacggccac ccttttctca cggaagttcc cgaaaacata atagtcaccc    6900
cttcacccat cgacgccaag agtagtaaga acaacgagga cgacgacgtc gtaggttgct    6960
tcgtgggctt ccacgcggac gagcccagaa gccgacacgt ggcttccctg ggaagctca     7020 gaggaataaa attcatgagc atattccggt ttaaggtgtg gtggaccact cactgggtcg    7080
gtagcaacgg acacgaactg gagcacgaga cacagatgat gcttctcgac aaaaacgacc    7140
agctcggacg cccctttgtg ttgattctcc cgatcctcca agcctcgttc cgagcctccc    7200
tgcaacccgg tttggatgat tacgtggacg tttgcatgga gagcgggtcg acacgtgtct    7260
gtggctccag cttcgggagc tgcttatacg tccacgttgg ccatgacccg tatcagttgc    7320
ttagagaagc aactaaagtc gttaggatgc atttggggac gttcaagctt ctcgaggaga    7380
aaaccgcgcc aggtatatac tcgccgctaa aaattcatca ccaaaattac tactgttttg    7440
ttttgttgga gtttttttt tttttttttt atatatataa taaggaggta ttttaaactt     7500
ttattgaatc tctcaactat tttttcactc tctttttttt acttatattt gactcataag    7560
aagcatcgaa ttgctatcaa attatattca ggcctgcaag ctttgaggga gtgtgtttat    7620
gtcatataat agaaataggg tatataaata aaggagaatc ctaacttttt ttggttgaca    7680
taaatttaaa tttaaatcct aaaacacgag taatttataa ttttaaggat taaatatgtt    7740
tttagttttt ttattttggt tgaatgttat tttagttttt cttttatact gtctaattta    7800
gttcataaag tttataaaaa aacgtctttt taattcctct ttacaactta aattttttaa    7860
aaatggtgca aaaattaggc agtaggtcta ggaactaaaa ataagattat ataaaaacta    7920
aaaacacaat attcactaat cttaatgaga tttttttaa aaaaatagta aaatttatt      7980 ttgtaaactg atttatttta tattgtagtg atcatagaca agtttggttg gtgtacatgg    8040
```

```
gacgcgtttt acttgaaggt gcatccctca ggtgtgtggg aagggtgaa agggttggtg      8100
gagggagggt gccctccagg gatggtccta atcgacgacg ggtggcaagc catttgtcac      8160
gacgaggacc ccataacgga ccaagagggt atgaagcgaa cctccgcagg ggagcaaatg      8220
ccatgcaggt tggtgaagtt ggaggaaaat tacaagttca gacagtattg tagtggaaag      8280
gattctgaga agggtatggg tgcctttgtt agggacttga aggaacagtt taggagcgtg      8340
gagcaggtgt atgtgtggca cgcgctttgt gggtattggg gtggggtcag acccaaggtt      8400
ccgggcatgc cccaggctaa ggttgtcact ccgaagctgt ccaatggact aaaattgaca      8460
atgaaggatt tagcggtgga taagatcgtc agtaacggag ttggactggt gccaccacac      8520
ctggctcacc ttttgtacga agggctccac tcccgtttgg aatctgcggg tattgacggt      8580
gttaaggttg acgttataca cgtaagtctc tactctgcat ttttgttttc tttttgacag      8640
tattgtctaa ccttttaact taattattta gatgaaaatt actcattttg attttgattt      8700
taatatggtg tttataggct tcagcaaaaa aaaaaaaaat ttggtgttta tagattagta      8760
atacatatag ttatagatta tagatgcctg tggaagaatt taagaattaa ttgatgatca      8820
aattgactac agtttagtta ctacagacta cagagtacct tagccatgtt tatgttctct      8880
gtagtgtatg tttttagttt ccaaggtaac attttgaact aaatatcaga attacttcgt      8940
aagtttaatt tgttgtcttt ggctacattt attcttgttt tctagtttgc tacgatactt      9000
gtacacggca agccatattt acaaatattt gtatgtggtg cttaaaaatt tgaaaggcaa      9060
attattcagt gaagtgtgta aaccgaaagt gaatatttct ttattggtgt atattaaaaa      9120
aactaagaat ttttatagta ttgatgactt aaaaaattta gattaaaaaa ctaataaaaa      9180
ataatgttga tgaatttaaa aatgtaatta ttgtataatt cgtttcctag gttggagaga      9240
atattgctta agttatataa agtaaataat tagaccaaaa tttgtttgac acaagtaatt      9300
tgacacttgc acacttggga ggcttaatca agatttgagt ttcaattttc aatttgagta      9360
tagagtcata acgagagatg ctactttatt acaaaatgaa atgagttaac ccggtgggag      9420
agaaatgagt tggatctcaa ataaaatacc ctagatatct cttggttaca tcaaaagaat      9480
ttttctttaa ttgtgacata taatggtaag atctatttaa gtggtgtaaa aagaaaaaaa      9540
aagagttgct aagttaaaga tctctaatat ttaatataat aatatatacc aatagtttta      9600
aattagaaaa atgatatatg ccttattgtt tggtatataa aatcaaaagg aaaaaataaa      9660
aataaaagag ataaagtgaa agaaagatct aataattaat aaataataca atgtcttaaa      9720
aagatatata aaaaataata taaaaataaa tatattatat aagtatataa attattatta      9780
ctaggggaaa gagatccacg tcttttctaaa aagaacttct ttttttaaat aaaacacaaa      9840
atgaaaaagg aaaagaacga gagaaagttg aaacaaaaat ggaagtgtgc aaatgtgcaa      9900
ttaactttat aaaatgatat atagttaaag atgatttaat ttttttaaaa aaagtaaaaa      9960
ccaaaaactt cgcattgtct ttattattaa ttatagatta tttagattaa gaaaaataaa     10020
tacaaataca gttttctata tgttagtgaa ctttgttgta aaaggttaca tgttactaaa     10080
tacacactag atgctctcat tatgtaaata tttgcaataa actacatgtt ctcatagtga     10140
tattttcttt aatactctat ataatttgtt taaatttatt agaaattagt aattttaatg     10200
agaagaactc atcaaaatgg atgatttta ataaatttca ataaaatgg ttaagaaaaa     10260
gagtaagtat tgttagcatt tcttattttg aaaatataat agacgttagg ttagcaacat     10320
cagcacgttc aatattcttt ctgtatttaa gtgttagtct aataggacca accatctgca     10380
tatatacact acggttgtca taattgcagg gttgaaactt gaaagccaaa ttctctcaac     10440
```

```
taaaaatgat ttatcatgag attgagaagt gtctcttccc ttggcacttg tatccttcgt    10500
aggaccgcat caagtgagta tacgaggatc ttgctaaatt aatattacaa ctcacaagta    10560
tcaacgaggt ttccaacttc gtttgatact tggaggtatc attttactat aaaaaaatgc    10620
catttactaa taatttaatg ttgggtttga aatcaagtt ggatcataat cagctatgaa     10680
gcccaagact ctataaagct agttctacat attaattggc ctcaagtggt ggctatacac    10740
aacggatttt tcaatatttc tattattata gcaaaacact aaactaaaca tagatcttga    10800
ttaaccatga ttacttagat gattttcaag tttaatattt cgtgatttgc attttttgcag   10860 ttgctcgaga tgctatccga ggaatacggt ggccgtgttg agctagccaa agcttattac    10920
aaagcgctca ctgcttcggt gaagaagcat ttcaaaggca atgggtcat tgcgagcatg     10980 gagcattgta atgacttctt tctccttggt accgaagcca tagcccttgg gcgcgtaggt    11040
aataatcatt ccaaattgca gcccttataa taaacaataa cattagtagt caaagtattt    11100
taacttgatt ggttgaatat tatctctgag ttattgtaaa ttttgtaaat ttttttaatag  11160 tgtctttaat tctcacggaa aaaaatatat taatagatct ttccaaaaca tcaaaacttt    11220
aacatacaca aatttttttgg agtttaatta tcatgtgtct tacacctaat taatcaaaaa   11280
tcatgtttga cataactttt aaaaaatttg tattaaaagt caataaatac gatagtttga    11340
gattgaacac aaagtaaaat tagtgtcaat gcattgtcta ttttctgaat tctccatcaa    11400
attttctaac ccataacaat acataaattc aggagatgat ttttggtgca ctgatccctc    11460
tggagatcca aatggcacgt attggctcca agggtgtcac atggtgcact gtgcctacaa    11520
cagcttgtgg atgggaatt ttattcagcc ggattgggac atgttccagt ccactcaccc    11580
ttgtgccgaa ttccatgcag cctctagggc catctctggt ggaccagttt acgttagtga    11640
ttgtgttgga aagcacaact tcaagttgct caagagcctc gctttgcctg atgggacgat    11700
tttgcgttgt caacactatg cactccccac acgagactgt ttgtttgaag accccttgca    11760
tgatgggaag acaatgctca aaatttggaa tctcaacaaa gtaagctacc ctcttttta    11820 aattatttt tcttttaatc cggtaaattt tttgtcagtg ttagggacta atcatctgag    11880 atgaaaaaa acaattcaag aggtcggctg ggaattaaac ttttgatcac atatttaaga   11940
agaaattctt acatgatcta gactttaaac taccatgatt gcaaacaatc tttgtccta    12000 ttgattattt ttttaattgg caaatgttag ttttgttaga aatgtcagtt tggaagattt    12060
gatatccttt cattttttcct tcttctttca tctttcttcc accactgaac caacctcgta   12120
tctttacatc ttattaaatt ttattttatt tttaatcgac aaatgttaat tattattatt    12180
gaattttatt aattgttttg agtgaaaatt agttgaaacc atgaaaaaat agtgatcatg    12240
caacttctaa tatttttttt catgttatga agcatgctta tttgtcaatt atatcagatc    12300 aattaattt ttaatcacac cataatgaca ttggaattat taataacctt tttatatttg    12360
ttttgttaca gtatacaggt gttttgggtc tatttaattg ccaaggaggt gggtggtgtc    12420
ccgtaactag gagaaacaag agtgcctctg aattttcaca aactgtgaca tgcttagcga    12480
gtcctcaaga cattgaatgg agcaatggga aaagcccaat atgcataaaa gggatgaatg    12540
tgtttgctgt atatttgttc aaggaccaca aactaaagct catgaaggca tcagagaaat    12600
tggaagtttc acttgagcca tttacttttg agctattgac agtgtctcca gtgattgtgc    12660
tgtcaaaaaa gttaattcaa tttgctccaa ttggattagt gaacatgctt aacactggtg    12720
gtgccattca gtccatggag tttgacaacc acatagatgg ggtcaaaatt ggggttaggg    12780
gttgtgggga gatgaaggtg tttgcatcag agaaaccagt tagttgcaaa ctagatgggg    12840
```
tagttgtaaa atttgattat gaggataaaa tgctgagagt gcaagttccc tggcctagtg   12900
cttcaaaatt gtcaatggtt gagttttat tttga                              12935

<210> SEQ ID NO 2
<211> LENGTH: 781
<212> TYPE: PRT
<213> ORGANISM: Glycine max

<400> SEQUENCE: 2

```
Met Ala Pro Ser Ile Ser Lys Thr Val Glu Leu Asn Ser Phe Gly Leu
1               5                   10                  15

Val Asn Gly Asn Leu Pro Leu Ser Ile Thr Leu Glu Gly Ser Asn Phe
            20                  25                  30

Leu Ala Asn Gly His Pro Phe Leu Thr Glu Val Pro Glu Asn Ile Ile
        35                  40                  45

Val Thr Pro Ser Pro Ile Asp Ala Lys Ser Ser Lys Asn Asn Glu Asp
    50                  55                  60

Asp Asp Val Val Gly Cys Phe Val Gly Phe His Ala Asp Glu Pro Arg
65                  70                  75                  80

Ser Arg His Val Ala Ser Leu Gly Lys Leu Arg Gly Ile Lys Phe Met
                85                  90                  95

Ser Ile Phe Arg Phe Lys Val Trp Trp Thr Thr His Trp Val Gly Ser
            100                 105                 110

Asn Gly His Glu Leu Glu His Glu Thr Gln Met Met Leu Leu Asp Lys
        115                 120                 125

Asn Asp Gln Leu Gly Arg Pro Phe Val Leu Ile Leu Pro Ile Leu Gln
    130                 135                 140

Ala Ser Phe Arg Ala Ser Leu Gln Pro Gly Leu Asp Asp Tyr Val Asp
145                 150                 155                 160

Val Cys Met Glu Ser Gly Ser Thr Arg Val Cys Gly Ser Ser Phe Gly
                165                 170                 175

Ser Cys Leu Tyr Val His Val Gly His Asp Pro Tyr Gln Leu Leu Arg
            180                 185                 190

Glu Ala Thr Lys Val Val Arg Met His Leu Gly Thr Phe Lys Leu Leu
        195                 200                 205

Glu Glu Lys Thr Ala Pro Val Ile Ile Asp Lys Phe Gly Trp Cys Thr
    210                 215                 220

Trp Asp Ala Phe Tyr Leu Lys Val His Pro Ser Gly Val Trp Glu Gly
225                 230                 235                 240

Val Lys Gly Leu Val Glu Gly Gly Cys Pro Pro Gly Met Val Leu Ile
                245                 250                 255

Asp Asp Gly Trp Gln Ala Ile Cys His Asp Glu Asp Pro Ile Thr Asp
            260                 265                 270

Gln Glu Gly Met Lys Arg Thr Ser Ala Gly Glu Gln Met Pro Cys Arg
        275                 280                 285

Leu Val Lys Leu Glu Glu Asn Tyr Lys Phe Arg Gln Tyr Cys Ser Gly
    290                 295                 300

Lys Asp Ser Glu Lys Gly Met Gly Ala Phe Val Arg Asp Leu Lys Glu
305                 310                 315                 320

Gln Phe Arg Ser Val Glu Gln Val Tyr Val Trp His Ala Leu Cys Gly
                325                 330                 335

Tyr Trp Gly Gly Val Arg Pro Lys Val Pro Gly Met Pro Gln Ala Lys
            340                 345                 350

Val Val Thr Pro Lys Leu Ser Asn Gly Leu Lys Leu Thr Met Lys Asp
```

```
                355                 360                 365
Leu Ala Val Asp Lys Ile Val Ser Asn Gly Val Gly Leu Val Pro Pro
370                 375                 380

His Leu Ala His Leu Leu Tyr Glu Gly Leu His Ser Arg Leu Glu Ser
385                 390                 395                 400

Ala Gly Ile Asp Gly Lys Val Asp Val Ile His Leu Leu Glu Met
                405                 410                 415

Leu Ser Glu Glu Tyr Gly Gly Arg Val Glu Leu Ala Lys Ala Tyr Tyr
                420                 425                 430

Lys Ala Leu Thr Ala Ser Val Lys Lys His Phe Lys Gly Asn Gly Val
                435                 440                 445

Ile Ala Ser Met Glu His Cys Asn Asp Phe Phe Leu Leu Gly Thr Glu
                450                 455                 460

Ala Ile Ala Leu Gly Arg Val Gly Asp Asp Phe Trp Cys Thr Asp Pro
465                 470                 475                 480

Ser Gly Asp Pro Asn Gly Thr Tyr Trp Leu Gln Gly Cys His Met Val
                485                 490                 495

His Cys Ala Tyr Asn Ser Leu Trp Met Gly Asn Phe Ile Gln Pro Asp
                500                 505                 510

Trp Asp Met Phe Gln Ser Thr His Pro Cys Ala Glu Phe His Ala Ala
                515                 520                 525

Ser Arg Ala Ile Ser Gly Gly Pro Val Tyr Val Ser Asp Cys Val Gly
                530                 535                 540

Lys His Asn Phe Lys Leu Leu Lys Ser Leu Ala Leu Pro Asp Gly Thr
545                 550                 555                 560

Ile Leu Arg Cys Gln His Tyr Ala Leu Pro Thr Arg Asp Cys Leu Phe
                565                 570                 575

Glu Asp Pro Leu His Asp Gly Lys Thr Met Leu Lys Ile Trp Asn Leu
                580                 585                 590

Asn Lys Tyr Thr Gly Val Leu Gly Leu Phe Asn Cys Gln Gly Gly Gly
                595                 600                 605

Trp Cys Pro Val Thr Arg Arg Asn Lys Ser Ala Ser Glu Phe Ser Gln
610                 615                 620

Thr Val Thr Cys Leu Ala Ser Pro Gln Asp Ile Glu Trp Ser Asn Gly
625                 630                 635                 640

Lys Ser Pro Ile Cys Ile Lys Gly Met Asn Val Phe Ala Val Tyr Leu
                645                 650                 655

Phe Lys Asp His Lys Leu Lys Leu Met Lys Ala Ser Glu Lys Leu Glu
                660                 665                 670

Val Ser Leu Glu Pro Phe Thr Phe Glu Leu Leu Thr Val Ser Pro Val
                675                 680                 685

Ile Val Leu Ser Lys Lys Leu Ile Gln Phe Ala Pro Ile Gly Leu Val
                690                 695                 700

Asn Met Leu Asn Thr Gly Gly Ala Ile Gln Ser Met Glu Phe Asp Asn
705                 710                 715                 720

His Ile Asp Val Val Lys Ile Gly Val Arg Gly Cys Gly Glu Met Lys
                725                 730                 735

Val Phe Ala Ser Glu Lys Pro Val Ser Cys Lys Leu Asp Gly Val Val
                740                 745                 750

Val Lys Phe Asp Tyr Glu Asp Lys Met Leu Arg Val Gln Val Pro Trp
                755                 760                 765

Pro Ser Ala Ser Lys Leu Ser Met Val Glu Phe Leu Phe
770                 775                 780
```

<210> SEQ ID NO 3
<211> LENGTH: 2346
<212> TYPE: DNA
<213> ORGANISM: Glycine max

<400> SEQUENCE: 3

| | | | | | |
|---|---|---|---|---|---|
| atggctccaa | gcataagcaa | aactgtggaa | ctaaattcat | ttggtcttgt | caacggtaat | 60 |
| ttgcctttgt | ccataacccct | agaaggatca | aatttcctcg | ccaacggcca | ccctttctc | 120 |
| acggaagttc | ccgaaaacat | aatagtcacc | ccttcaccca | tcgacgccaa | gagtagtaag | 180 |
| aacaacgagg | acgacgacgt | cgtaggttgc | ttcgtgggct | ccacgcgga | cgagcccaga | 240 |
| agccgacacg | tggcttccct | ggggaagctc | agaggaataa | aattcatgag | catattccgg | 300 |
| tttaaggtgt | ggtggaccac | tcactgggtc | ggtagcaacg | gacacgaact | ggagcacgag | 360 |
| acacagatga | tgcttctcga | caaaaacgac | cagctcggac | gccccttgt | gttgattctc | 420 |
| ccgatcctcc | aagcctcgtt | ccgagcctcc | ctgcaacccg | gtttggatga | ttacgtggac | 480 |
| gtttgcatgg | agagcgggtc | gacacgtgtc | tgtggctcca | gcttcgggag | ctgcttatac | 540 |
| gtccacgttg | gccatgaccc | gtatcagttg | cttagagaag | caactaaagt | cgttaggatg | 600 |
| catttgggga | cgttcaagct | tctcgaggag | aaaaccgcgc | cagtgatcat | agacaagttt | 660 |
| ggttggtgta | catgggacgc | gttttacttg | aaggtgcatc | cctcaggtgt | gtgggaaggg | 720 |
| gtgaaagggt | tggtggaggg | agggtgccct | ccagggatgg | tcctaatcga | cgacgggtgg | 780 |
| caagccattt | gtcacgacga | ggacccccata | acggaccaag | agggtatgaa | gcgaacctcc | 840 |
| gcaggggagc | aaatgccatg | caggttggtg | aagttggagg | aaaattacaa | gttcagacag | 900 |
| tattgtagtg | aaaggattc | tgagaagggt | atgggtgcct | ttgttaggga | cttgaaggaa | 960 |
| cagtttagga | gcgtggagca | ggtgtatgtg | tggcacgcgc | tttgtgggta | ttggggtggg | 1020 |
| gtcagaccca | aggttccggg | catgcccccag | gctaaggttg | tcactccgaa | gctgtccaat | 1080 |
| ggactaaaat | tgacaatgaa | ggatttagcg | gtggataaga | tcgtcagtaa | cggagttgga | 1140 |
| ctggtgccac | cacacctggc | tcacctttg | tacgaagggc | tccactcccg | tttggaatct | 1200 |
| gcgggtattg | acggtgttaa | ggttgacgtt | atacacttgc | tcgagatgct | atccgaggaa | 1260 |
| tacggtggcc | gtgttgagct | agccaaagct | tattacaaag | cgctcactgc | ttcggtgaag | 1320 |
| aagcatttca | aggcaatgg | ggtcattgcg | agcatggagc | attgtaatga | cttctttctc | 1380 |
| cttggtaccg | aagccatagc | ccttgggcgc | gtaggagatg | attttggtg | cactgatccc | 1440 |
| tctgagatc | caaatggcac | gtattggctc | caagggtgtc | acatggtgca | ctgtgcctac | 1500 |
| aacagcttgt | ggatggggaa | ttttattcag | ccggattggg | acatgttcca | gtccactcac | 1560 |
| ccttgtgccg | aattccatgc | agcctctagg | gccatctctg | gtggaccagt | ttacgttagt | 1620 |
| gattgtgttg | aaagcacaa | cttcaagttg | ctcaagagcc | tcgctttgcc | tgatgggacg | 1680 |
| attttgcgtt | gtcaacacta | tgcactcccc | acacgagact | gtttgtttga | agaccccttg | 1740 |
| catgatggga | agacaatgct | caaaatttgg | aatctcaaca | aatatacagg | tgttttgggt | 1800 |
| ctatttaatt | gccaaggagg | tgggtggtgt | cccgtaacta | ggagaaacaa | gagtgcctct | 1860 |
| gaattttcac | aaactgtgac | atgcttagcg | agtcctcaag | acattgaatg | gagcaatggg | 1920 |
| aaaagcccaa | tatgcataaa | agggatgaat | gtgtttgctg | tatatttgtt | caaggaccac | 1980 |
| aaactaaagc | tcatgaaggc | atcagagaaa | ttggaagttt | cacttgagcc | atttactttt | 2040 |
| gagctattga | cagtgtctcc | agtgattgtg | ctgtcaaaaa | agttaattca | atttgctcca | 2100 |
| attggattag | tgaacatgct | taacactggt | ggtgccattc | agtccatgga | gtttgacaac | 2160 |

-continued

```
cacatagatg tggtcaaaat tggggttagg ggttgtgggg agatgaaggt gtttgcatca    2220
gagaaaccag ttagttgcaa actagatggg gtagttgtaa aatttgatta tgaggataaa    2280
atgctgagag tgcaagttcc ctggcctagt gcttcaaaat tgtcaatggt tgagtttta    2340 ttttga                                                               2346
```

<210> SEQ ID NO 4
<211> LENGTH: 2346
<212> TYPE: DNA
<213> ORGANISM: Glycine max

<400> SEQUENCE: 4

```
atggctccaa gcataagcaa aactgtggaa ctaaattcat ttggtcttgt caacggtaat      60
ttgcctttgt cctaacccct agaaggatca aatttcctcg ccaacggcca cccttttctc    120
acggaagttc ccgaaaacat aatagtcacc ccttcaccca tcgacgccaa gagtagtaag    180
aacaacgagg acgacgacgt cgtaggttgc ttcgtgggct ccacgcggga cgagcccaga    240
agccgacacg tggcttccct ggggaagctc agaggaataa aattcatgag catattccgg    300
tttaaggtgt ggtggaccat tcactgggtc ggtagcaacg acacgaact ggagcacgag     360 acacagatga tgcttctcga caaaaacgac cagctcggac gccccttttgt gttgattctc    420 ccgatcctcc aagcctcgtt ccgagcctcc ctgcaacccg gtttggatga ttacgtggac    480
gtttgcatgg agagcgggtc gacacgtgtc tgtggctcca gcttcgggag ctgcttatac    540
gtccacgttg gccatgaccc gtatcagttg cttagagaag caactaaagt cgttaggatg    600
catttgggga cgttcaagct tctcgaggag aaaaccgcgc cagtgatcat agacaagttt    660
ggttggtgta catgggacgc gttttacttg aaggtgcatc cctcaggtgt gtgggaaggg    720
gtgaaagggt tggtggaggg agggtgccct ccagggatgg tcctaatcga cgacgggtgg    780
caagccattt gtcacgacga ggaccccata acggaccaag agggtatgaa gcgaacctcc    840 gcagggggagc aaatgccatg caggttggtg aagttggagg aaaattacaa gttcagacag    900
tattgtagtg aaaggattc tgagaagggt atgggtgcct tgttaggga cttgaaggaa     960 cagtttagga gcgtggagca ggtgtatgtg tggcacgcgc tttgtgggta ttggggtggg    1020
gtcagaccca aggttccggg catgccccag gctaaggttg tcactccgaa gctgtccaat    1080
ggactaaaat tgacaatgaa ggatttagcg gtggataaga tcgtcagtaa cggagttgga    1140
ctggtgccac cacacctggc tcaccttttg tacgaagggc tccactcccg tttggaatct    1200
gcgggtattg acgtgttaa ggttgacgtt atacacttgc tcgagatgct atccgaggaa    1260
tacggtggcc gtgttgagct agccaaagct tattacaaag cgctcactgc ttcggtgaag    1320
aagcatttca aggcaatggg ggtcattgcg agcatggagc attgtaatga cttcttcc      1380 cttggtaccg aagccatagc ccttgggcgc gtaggagatg attttttggtg cactgatccc   1440 tctgagatc caaatggcac gtattggctc caagggtgtc acatggtgca ctgtgcctac    1500
aacagcttgt ggatggggaa ttttattcag ccggattggg acatgttcca gtccactcac    1560
ccttgtgccg aattccatgc agcctctagg gccatctctg gtggaccagt ttacgttagt    1620
gattgtgttg gaaagcacaa cttcaagttg ctcaagagcc tcgctttgcc tgatgggacg    1680
attttgcgtt gtcaacacta tgcactcccc acacgagact gtttgtttga agacccctg     1740 catgatggga agacaatgct caaaatttgg aatctcaaca aatatacagg tgttttgggt    1800
ctatttaatt gccaaggagg tgggtggtgt ccgtaacta ggagaaacaa gagtgcctct    1860
gaattttcac aaactgtgac atgcttagcg agtcctcaag acattgaatg gagcaatggg    1920
```

-continued

```
aaaagcccaa tatgcataaa agggatgaat gtgtttgctg tatatttgtt caaggaccac   1980
aaactaaagc tcatgaaggc atcagagaaa ttggaagttt cacttgagcc atttactttt   2040
gagctattga cagtgtctcc agtgattgtg ctgtcaaaaa agttaattca atttgctcca   2100
attggattag tgaacatgct taacactggt ggtgccattc agtccatgga gtttgacaac   2160
cacatagatg tggtcaaaat tggggttagg ggttgtgggg agatgaaggt gtttgcatca   2220
gagaaaccag ttagttgcaa actagatggg gtagttgtaa aatttgatta tgaggataaa   2280
atgctgagag tgcaagttcc ctggcctagt gcttcaaaat tgtcaatggt tgagttttta   2340
ttttga                                                              2346
```

<210> SEQ ID NO 5
<211> LENGTH: 781
<212> TYPE: PRT
<213> ORGANISM: Glycine max

<400> SEQUENCE: 5

```
Met Ala Pro Ser Ile Ser Lys Thr Val Glu Leu Asn Ser Phe Gly Leu
1               5                   10                  15

Val Asn Gly Asn Leu Pro Leu Ser Ile Thr Leu Glu Gly Ser Asn Phe
            20                  25                  30

Leu Ala Asn Gly His Pro Phe Leu Thr Glu Val Pro Glu Asn Ile Ile
        35                  40                  45

Val Thr Pro Ser Pro Ile Asp Ala Lys Ser Ser Lys Asn Asn Glu Asp
    50                  55                  60

Asp Asp Val Val Gly Cys Phe Val Gly Phe His Ala Asp Glu Pro Arg
65                  70                  75                  80

Ser Arg His Val Ala Ser Leu Gly Lys Leu Arg Gly Ile Lys Phe Met
                85                  90                  95

Ser Ile Phe Arg Phe Lys Val Trp Trp Thr Ile His Trp Val Gly Ser
            100                 105                 110

Asn Gly His Glu Leu Glu His Glu Thr Gln Met Met Leu Leu Asp Lys
        115                 120                 125

Asn Asp Gln Leu Gly Arg Pro Phe Val Leu Ile Leu Pro Ile Leu Gln
    130                 135                 140

Ala Ser Phe Arg Ala Ser Leu Gln Pro Gly Leu Asp Asp Tyr Val Asp
145                 150                 155                 160

Val Cys Met Glu Ser Gly Ser Thr Arg Val Cys Gly Ser Ser Phe Gly
                165                 170                 175

Ser Cys Leu Tyr Val His Val Gly His Asp Pro Tyr Gln Leu Leu Arg
            180                 185                 190

Glu Ala Thr Lys Val Val Arg Met His Leu Gly Thr Phe Lys Leu Leu
        195                 200                 205

Glu Glu Lys Thr Ala Pro Val Ile Ile Asp Lys Phe Gly Trp Cys Thr
    210                 215                 220

Trp Asp Ala Phe Tyr Leu Lys Val His Pro Ser Gly Val Trp Glu Gly
225                 230                 235                 240

Val Lys Gly Leu Val Glu Gly Gly Cys Pro Pro Gly Met Val Leu Ile
                245                 250                 255

Asp Asp Gly Trp Gln Ala Ile Cys His Asp Glu Asp Pro Ile Thr Asp
            260                 265                 270

Gln Glu Gly Met Lys Arg Thr Ser Ala Gly Glu Gln Met Pro Cys Arg
        275                 280                 285

Leu Val Lys Leu Glu Glu Asn Tyr Lys Phe Arg Gln Tyr Cys Ser Gly
    290                 295                 300
```

-continued

```
Lys Asp Ser Glu Lys Gly Met Gly Ala Phe Val Arg Asp Leu Lys Glu
305                 310                 315                 320

Gln Phe Arg Ser Val Glu Gln Val Tyr Val Trp His Ala Leu Cys Gly
                325                 330                 335

Tyr Trp Gly Gly Val Arg Pro Lys Val Pro Gly Met Pro Gln Ala Lys
            340                 345                 350

Val Val Thr Pro Lys Leu Ser Asn Gly Leu Lys Leu Thr Met Lys Asp
        355                 360                 365

Leu Ala Val Asp Lys Ile Val Ser Asn Gly Val Gly Leu Val Pro Pro
370                 375                 380

His Leu Ala His Leu Leu Tyr Glu Gly Leu His Ser Arg Leu Glu Ser
385                 390                 395                 400

Ala Gly Ile Asp Gly Val Lys Val Asp Val Ile His Leu Leu Glu Met
                405                 410                 415

Leu Ser Glu Glu Tyr Gly Gly Arg Val Glu Leu Ala Lys Ala Tyr Tyr
            420                 425                 430

Lys Ala Leu Thr Ala Ser Val Lys His Phe Lys Gly Asn Gly Val
        435                 440                 445

Ile Ala Ser Met Glu His Cys Asn Asp Phe Phe Leu Leu Gly Thr Glu
450                 455                 460

Ala Ile Ala Leu Gly Arg Val Gly Asp Asp Phe Trp Cys Thr Asp Pro
465                 470                 475                 480

Ser Gly Asp Pro Asn Gly Thr Tyr Trp Leu Gln Gly Cys His Met Val
                485                 490                 495

His Cys Ala Tyr Asn Ser Leu Trp Met Gly Asn Phe Ile Gln Pro Asp
            500                 505                 510

Trp Asp Met Phe Gln Ser Thr His Pro Cys Ala Glu Phe His Ala Ala
        515                 520                 525

Ser Arg Ala Ile Ser Gly Gly Pro Val Tyr Val Ser Asp Cys Val Gly
530                 535                 540

Lys His Asn Phe Lys Leu Leu Lys Ser Leu Ala Leu Pro Asp Gly Thr
545                 550                 555                 560

Ile Leu Arg Cys Gln His Tyr Ala Leu Pro Thr Arg Asp Cys Leu Phe
                565                 570                 575

Glu Asp Pro Leu His Asp Gly Lys Thr Met Leu Lys Ile Trp Asn Leu
            580                 585                 590

Asn Lys Tyr Thr Gly Val Leu Gly Leu Phe Asn Cys Gln Gly Gly Gly
        595                 600                 605

Trp Cys Pro Val Thr Arg Arg Asn Lys Ser Ala Ser Glu Phe Ser Gln
610                 615                 620

Thr Val Thr Cys Leu Ala Ser Pro Gln Asp Ile Glu Trp Ser Asn Gly
625                 630                 635                 640

Lys Ser Pro Ile Cys Ile Lys Gly Met Asn Val Phe Ala Val Tyr Leu
                645                 650                 655

Phe Lys Asp His Lys Leu Lys Leu Met Lys Ala Ser Glu Lys Leu Glu
            660                 665                 670

Val Ser Leu Glu Pro Phe Thr Phe Glu Leu Leu Thr Val Ser Pro Val
        675                 680                 685

Ile Val Leu Ser Lys Lys Leu Ile Gln Phe Ala Pro Ile Gly Leu Val
690                 695                 700

Asn Met Leu Asn Thr Gly Gly Ala Ile Gln Ser Met Glu Phe Asp Asn
705                 710                 715                 720

His Ile Asp Val Val Lys Ile Gly Val Arg Gly Cys Gly Glu Met Lys
                725                 730                 735
```

```
Val Phe Ala Ser Glu Lys Pro Val Ser Cys Lys Leu Asp Gly Val Val
            740                 745                 750

Val Lys Phe Asp Tyr Glu Asp Lys Met Leu Arg Val Gln Val Pro Trp
        755                 760                 765

Pro Ser Ala Ser Lys Leu Ser Met Val Glu Phe Leu Phe
    770                 775                 780

<210> SEQ ID NO 6
<211> LENGTH: 23
<212> TYPE: DNA
<213> ORGANISM: Glycine max

<400> SEQUENCE: 6
gagtctcata ttgtacatgg tag                                           23

<210> SEQ ID NO 7
<211> LENGTH: 22
<212> TYPE: DNA
<213> ORGANISM: Glycine max

<400> SEQUENCE: 7
gcaattcgat gcttcttatg ag                                            22

<210> SEQ ID NO 8
<211> LENGTH: 19
<212> TYPE: DNA
<213> ORGANISM: Glycine max

<400> SEQUENCE: 8
cccaccatgt caccacacc                                                19

<210> SEQ ID NO 9
<211> LENGTH: 21
<212> TYPE: DNA
<213> ORGANISM: Glycine max

<400> SEQUENCE: 9
ggtgatgaat ttttagcggc g                                             21

<210> SEQ ID NO 10
<211> LENGTH: 26
<212> TYPE: DNA
<213> ORGANISM: Glycine max

<400> SEQUENCE: 10
gcgggcgttg ctaccgaccc agtgaa                                        26

<210> SEQ ID NO 11
<211> LENGTH: 34
<212> TYPE: DNA
<213> ORGANISM: Glycine max

<400> SEQUENCE: 11
gcgggcaggg cggcgttgct accgacccag cgag                               34

<210> SEQ ID NO 12
<211> LENGTH: 25
<212> TYPE: DNA
<213> ORGANISM: Glycine max

<400> SEQUENCE: 12
cagaggaata aaattcatga gcata                                         25
```

RS2 MUTANT ALLELE, PERFECT MOLECULAR MARKERS, AND LOW RAFFINOSE/STACHYOSE SOYBEAN GERMPLASM

CROSS-REFERENCE TO RELATED APPLICATIONS

This application claims the benefit under 35 U.S.C. 1.19(e) of U.S. provisional 61/362,738, filed Jul. 9, 2010, the contents of which are incorporated by reference herein.

BACKGROUND OF THE INVENTION

1. Field of the Invention

The invention relates to mutant alleles of the soybean raffinose synthase 2 gene, RS2, the use of the mutant alleles to produce soybean with a reduced raffinose and stachyose phenotype, and methods for detecting the mutant alleles in breeding reduced raffinose and stachyose soybean.

2. Description of the Prior Art

Soybean is an important source of vegetable oil and high protein meal that is incorporated into many foods and feeds, and the use of soybean meal by the food industry is increasing. However, anti-nutritional compounds such as phytate, raffinose family oligosaccharides, and allergenic proteins that accumulate during normal soybean seed development limit the extent to which soybean meal can be included in livestock diet formulations. Raffinose synthase catalyzes the biochemical reaction to produce raffinose from sucrose and galactinol. Stachyose is formed in a stepwise reaction utilizing raffinose and galactinol as substrates.

Low raffinose and stachyose has been identified as a desirable seed phenoytpe in soybean. Monogastric animals that consume soybean meal lack the enzymes which are necessary to digest either of these oligosaccharides, thereby effectively reducing the metabolizable energy of the meal. Since raffinose and stachyose are considered anti-nutritional components of soybean meal, reducing these oligosaccharide components enhances the value of the soybean meal. Kerr and Sebastian (U.S. Pat. No. 5,710,365) previously described the production of low raffinose and stachyose soybean. Upon subsequent analysis, the PI 200508 allele of the soybean raffinose synthase gene desginated RS2 of Kerr and Sebastian was associated with the increased sucrose and low raffinose and stachyose seed phenotype [Dierking and Bilyeu: Association of a soybean raffinose synthase gene with low raffinose and stachyose seed phenotype. *The Plant Genome* 2008, 1(2):135-145].

However, despite these and other advances, the need remains for improved soybean having reduced raffinose and stachyose content.

SUMMARY OF THE INVENTION

We have now discovered a novel mutation in the gene encoding the raffinose synthase 2 enzyme, RS2, in soybean, *Glycine max* (L.) Merr., which is associated with a reduced raffinose and stachyose seed phenotype. Soybean homozygous for a mutant allele of the RS2 gene which encodes an amino acid change to isoleucine at position 107 of the enzyme's amino acid sequence exhibit significantly reduced seed raffinose and stachyose content, and increased seed sucrose content. Nucleic acid samples of soybean may be assayed for the presence of this mutant allele, and soybean containing the allele may be selected for breeding to generate reduced raffinose and stachyose soybean lines. Alternatively, the mutation may be detected by analysis of the raffinose synthase 2 enzyme produced in the soybean to determine the presence of either an isoleucine or a threonine at amino acid 107. Molecular markers have been developed for detecting the presence or absence of the mutant allele.

In accordance with this discovery, it is an object of this invention to provide a mutant allele of the gene encoding soybean raffinose synthase 2 enzyme, RS2, which mutant allele is associated with reduced seed content of raffinose and stachyose.

Another object of this invention is to provide a mutant allele of the gene encoding raffinose synthase 2 enzyme, RS2, in soybean, which mutant allele encodes an isoleucine at amino acid 107 of the enzyme's amino acid sequence.

A further object of this invention is to provide a method for identifying soybean germplasm containing this mutant raffinose synthase 2 enzyme, RS2, allele for use in breeding to develop low raffinose and stachyose soybean lines.

Still another object of this invention is to provide molecular markers for detecting the mutant raffinose synthase 2 enzyme, RS2, allele associated with reduced raffinose and stachyose seed content.

Other objects and advantages of this invention will become readily apparent from the ensuing description.

BRIEF DESCRIPTION OF THE DRAWINGS

FIG. 1 shows the coding sequence of the Williams 82 (wild-type) RS2 allele, SEQ ID NO: 3.

FIG. 2 shows the amino acid sequence of the Williams 82 (wild-type) RS2 enzyme, SEQ ID NO: 2.

FIG. 3 shows the coding sequence of the mutant RS2 allele from line 397, SEQ ID NO: 4.

FIG. 4 shows the amino acid sequence of the mutant RS2 enzyme, SEQ ID NO: 5.

DEFINITIONS

Allele: the term coined by Bateson and Saunders (1902) for characters which are alternative to one another in Mendelian inheritance (Gk. Allelon, one another; morphe, form). Now the term allele is used for two or more alternative forms of a gene resulting in different gene products and thus different phenotypes. In a haploid set of chromosomes there is only one allele at its specific locus. Diploid organisms have 2 alleles at a given locus, and if they are homozygous for a defined gene, both alleles are identical. However, if heterozygous for a defined gene they have one normal and one mutant allele. A single allele for each gene locus is inherited separately from each parent (e.g., at a locus for eye color the allele might result in blue or brown eyes). An organism is homozygous for a gene if the alleles are identical, and heterozygous if they are different. (Birgid Schlindwein's Hypermedia Glossary of Genetic Terms).

Amplicon: a term to define the amplification product generated by the polymerase chain reaction. The physical boundaries of an amplicon extend to the base sequence at the 5' ends of each of a pair of primers (short, 18-20 oligonucleotides) in the reaction.

Centimomorgan (cM): a unit to measure the recombination frequency. One centimorgan is equal to a 1% chance that a marker at one genetic locus will be separated from a marker at a second locus due to crossing over in a single generation. In human beings, 1 centimorgan is equivalent, on average, to 1 million base pairs. (Birgid Schlindwein's Hypermedia Glossary of Genetic Terms).

Crossing over: the term coined by Morgan and Cattell (1912) for the occurrence of new combinations of linked characters. With the acceptance of the chromosome theory, the term is applied to the breaking during meiosis of one maternal and one paternal chromosome, the exchange of corresponding sections of DNA, and the rejoining of the chromosomes. This process can result in an exchange of alleles between chromosomes and gives rise to new character combinations. (Birgid Schlindwein's Hypermedia Glossary of Genetic Terms).

DNA or RNA sequence: a linear series of nucleotides connected one to the other by phosphodiester bonds between the 3' and 5' carbons of adjacent pentoses.

Genotype: the term proposed by Johannsen (1909) for the hereditary constitution of an individual, or of particular nuclei within its cells. (Birgid Schlindwein's Hypermedia Glossary of Genetic Terms).

Identity by descent: two alleles at a single locus are identical by descent if there are identical copies of the same allele in some earlier generation, i.e., both are copies that arose by DNA replication from the same ancestral sequence without any intervening mutation. The organism is homozygous for this defined locus.

Identity by type: two alleles at a single locus are identical by type, (i.e. "the same") if they have the same phenotypic effects.

Locus: the position of a gene on a chromosome or other chromosome markers; also, the DNA at that position. The use of the term locus is sometimes restricted to main regions of DNA that are expressed. (Birgid Schlindwein's Hypermedia Glossary of Genetic Terms).

Marker: an identifiable physical location on a chromosome (e.g., restriction enzyme cutting site, gene, minisatellite, microsatellite) whose inheritance can be monitored. Markers can be expressed regions of DNA (genes) or some segment of DNA with no known coding function but whose pattern of inheritance can be determined. (Birgid Schlindwein's Hypermedia Glossary of Genetic Terms).

Nucleic acid: a deoxyribonucleotide or ribonucleotide polymer in either single- or double-stranded form, including known analogs of natural nucleotides unless otherwise indicated.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

Oligonucleotide: a single-stranded nucleic acid ranging in length from 2 to about 500 bases, usually 2-100 bases.

Phenotype: the term coined by Johannsen (1909) for the appearance (Gk. phainein, to appear) of an organism with respect to a particular character or group of characters (physical, biochemical, and physiologic), as a result of the interaction of its genotype and its environment. Often used to define the consequences of a particular mutation. (Birgid Schlindwein's Hypermedia Glossary of Genetic Terms).

Polymorphic marker or site: the locus at which divergence occurs. Preferred markers have at least two alleles, each occurring at frequency of greater than 1%, and more preferably greater than 10% or 20% of a selected population. A polymorphic locus may be as small as one base pair, such as a single nucleotide polymorphism (SNP). Polymorphic markers include detection of restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild-type form. Diploid organisms may be homozygous or heterozygous for allelic forms. A diallelic polymorphism has two forms. A triallelic polymorphism has three forms (U.S. Pat. No. 6,368,799).

Probe: a DNA fragment or an oligonucleotide capable of binding to a target nucleic acid of complementary sequence through one or more types of chemical bonds, by hybridization or complementary base pairing, usually through hydrogen bond formation. Oligonucleotides probes are often 10-50 or 15-30 bases long. An oligonucleotide probe may include natural (i.e. A, G, C, or T) or modified bases (7-deazaguanosine, inosine, etc.).

Recombination: the process by which progeny derive a combination of linked genes different from that of either parent. In higher organisms, this can occur by crossing over between their loci during meiosis. Recombination may come about through random orientation of non-homologous chromosome pairs on the meiotic spindles, from crossing-over between homologous chromosomes, from gene conversion, or by other means. (Birgid Schlindwein's Hypermedia Glossary of Genetic Terms).

Single nucleotide polymorphism (SNP): occurrence of a polymorphic site occupied by a single nucleotide, constituting the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site.

Specific hybridization: binding, duplexing, or hybridizing of a molecule only to a particular nucleotide sequence under stringent conditions such that the probe will hybridize to its target subsequence, but not to other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. A perfectly matched probe has a sequence perfectly complementary to a particular target sequence (U.S. Pat. No. 6,368,799).

Transition: the term proposed by Freese (1959) for a mutation caused by the substitution in DNA or RNA of one purine by the other, and similarly with the pyrimidines. (Birgid Schlindwein's Hypermedia Glossary of Genetic Terms).

Transversion: the term proposed by Freese (1959) for a mutation caused by the substitution of a purine for a pyrimidine, and vice versa, in DNA or RNA. (Birgid Schlindwein's Hypermedia Glossary of Genetic Terms).

DETAILED DESCRIPTION OF THE INVENTION

In the following description, the nomenclature used to define the peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The instant invention provides mutants or variants of the soybean raffinose synthase 2 enzyme, RS2, which are associated with a significantly reduced raffinose and stachyose seed phenotype in comparison to normal or wild-type cultivars. As described in greater detail below, a novel, mutant soybean line, designated line 397, was produced by chemical mutagenesis of an agronomically recognized cultivar, Williams 82, which exhibits a typical raffinose and stachyose seed content. Line 397 contains a mutant RS2 allele which is responsible for a threonine to isoleucine change at position 107 of the enzyme's amino acid sequence, which change we have associated with a significantly reduced raffinose and stachyose seed content, and a significantly increased sucrose seed content, in comparison to the original Williams 82 line. Seed of soybean homozygous for the mutant RS2 allele of this invention exhibit on average, an approximate 3-fold reduction in raffinose content, a 2-fold reduction in stachyose, and an increase in sucrose of approximately 118% or 1.2 fold, relative to seed that are heterozygous or homozygous for the Williams 82 line RS2 allele. Thus, the detection of soybean homozygous for a mutant RS2 allele which encodes a threonine to isoleucine change at position 107 of the RS2 amino acid sequence is indicative of reduced raffinose and stachyose seed content, and an increased seed sucrose content in the soybean. Accordingly, assays for the detection of this mutant RS2 allele, or the altered RS2 enzyme per se, may be used to select germplasm for breeding to produce lines which are homozygous for the mutant allele and have a low raffinose/stachyose phenotype.

The coding sequence of the soybean RS2 gene has been sequenced. A partial genomic sequence, which includes the entire coding sequence of the RS2 allele, as well as the corresponding amino acid sequence of the encoded RS2 enzyme, for soybean cultivar Williams 82 (the consensus wild-type) have been deposited in GenBank under accession numbers EU651888 (SEQ ID NO: 1) and ACD13461 (SEQ ID NO: 2), respectively. The contents of each of these GenBank accessions are incorporated by reference herein. The coding sequence corresponds to nucleotides 570-1212 (exon 1) plus 1829-2421 (exon 2), 4681-4858 (exon 3), 5253-5620 (exon 4) and 6192-6755 (exon 5) of SEQ ID NO: 1, and the complete coding sequence is shown in FIG. 1 as SEQ ID NO: 3. The Williams 82 RS2 allele contains a cytosine at nucleotide 320 of the coding sequence (exon 1, and corresponds to base 889 of the genomic sequence SEQ ID NO: 1) and a corresponding ACT codon at nucleotides 319-321 (codon 107 of the coding sequence), encoding a threonine at amino acid 107 of the RS2 enzyme. The coding sequence of the RS2 allele of the mutant soybean line 397 has also been sequenced. This mutant RS2 allele is the same as that of soybean cultivar Williams 82 except that it contains a single nucleotide polymorphism (SNP) at nucleotide 320 of the coding sequence wherein the cytosine has been changed to thymine, creating an ATT codon at nucleotides 319-321. No other sequence differences were observed between the mutant RS2 allele and the Williams 82 RS2 allele. The coding sequence of the mutant RS2 allele containing the c320t SNP is represented as SEQ ID NO: 4. This mutant allele encodes an isoleucine at amino acid 107 of the RS2 enzyme, which is represented as SEQ ID NO: 5. Although the c320t SNP has been described in relationship to the RS2 coding sequence of SEQ ID NOs: 3 and 4, the invention is not limited to these specific nucleotide sequences. For example, it is envisioned that the RS2 coding sequence may include any codon (e.g., ATT, ATC or ATA) at positions 319-321 which encodes an isoleucine at amino acid 107 of RS2. Moreover, the RS2 coding sequence may encompass other polymorphisms or other RS2 alleles, provided that the coding sequence includes an SNP encoding an isoleucine at position 107 of the enzyme's amino acid sequence. It is envisioned that any mutant allele of RS2 in soybean having a nucleotide sequence encoding an isoleucine at position 107 of the enzyme's amino acid sequence, will be associated with a significantly reduced raffinose and stachyose seed content, and a significantly increased sucrose seed content, in comparison to any parent line lacking the SNP, including the Williams 82 line.

The mutant RS2 allele of this invention may be detected by assaying a sample of nucleic acid molecules from the germplasm of soybean, *Glycine max* (L.) Merr., for the presence of an SNP encoding an isoleucine at position 107 of the enzyme's amino acid sequence. More specifically, the mutant allele is indicated by the presence of a thymine at nucleotide 319 of the RS2 coding sequence. Suitable nucleic acids for use in the assay include genomic DNA, cDNA, or RNA, as well as nucleic acids that encompass, or are encompassed by, SEQ ID NOs: 3 or 4, or the complement thereof. However, the use of genomic DNA molecules is preferred. It is also envisioned that the SNP may also be detected by analysis of the encoded gene product, i.e., the amino acid sequence of the RS2 enzyme in a sample obtained from a subject soybean plant to detect an isoleucine at position 107. Sample materials which may be collected from the soybean for the assays include, but are not limited to, seeds, leaves, cells or other biological samples from the subject.

The presence of the mutant allele can be determined by any of a number of molecular marker assays. These assays may use otherwise known techniques, including direct sequencing of the nucleic acids in the sample, or using probes which overlap the position of the above-mentioned c320t SNP in the coding sequence of the gene encoding RS2. For example, suitable assays include, but are not limited to, ligase based methods such as described by Barany et al. (1997) WO 97/31256 and Chen et al. Genome Res. 1998; 8(5):549-556; mass-spectroscopy-based methods by Monforte (1998) WO 98/12355, Turano et al. (1998) WO 98/14616 and Ross et al. (1997) Anal. Chem. 15:4197-4202; PCR-based methods such as disclosed by Hauser, et al. (1998) Plant J. 16:117-125; exonuclease-based methods by Mundy U.S. Pat. No. 4,656, 127; dideoxynucleotide-based methods by Cohen et al. WO 91/02087; Genetic Bit Analysis or GBA by Goelet et al. WO 92/15712; Oligonucleotide Ligation Assays or OLAs by Landegren et al. (1988) Science 241:1077-1080 and Nickerson et al. (1990) Proc. Natl. Acad. Sci. (USA) 87:8923-8927; and primer-guided nucleotide incorporation procedures by Prezant et al. (1992) Hum. Mutat. 1:159-164; Ugozzoli et al. (1992) GATA 9:107-112; Nyreen et al. (1993) Anal. Biochem. 208:171-175, all of which are incorporated herein by reference. The presence of the SNP on the RS2 gene may also be detected by assaying for the same nucleotides described above at the locus corresponding to nucleotide 320 of the RS2 coding sequence in an RNA molecule which is a transcript of a sequence encompassed by, or encompassing, the complementary strand to SEQ ID NOs: 3 or 4. Alternatively, the SNP may be detected in the DNA strand complementary to SEQ ID NOs: 3 or 4 by assaying for the complementary nucleotides at the locus corresponding to nucleotide 320 of the RS2 coding sequence. Northern Blot analysis is preferred for analysis of RNA samples. The nucleic acid molecule comprising the mutant RS2 allele may also be used in a hybridization assay to detect mutant alleles in other soybean samples or to produce hybridization probes in such assays.

In accordance with a preferred embodiment, the presence of the mutant allele is detected by PCR amplification or melting curve analysis as described in Example 1. It is envisioned that a variety of primers and PCR assays may be suitable for use in the amplification, although preferred primers for use herein are described in Example 1.

As noted above, it is envisioned that the SNP on the RS2 gene may also be detected by analysis of the RS2 enzyme product. For example, the threonine to isoleucine substitution at amino acid 107 of RS2 caused by the SNP, may be identified by contacting the biological samples with immunolabelling agents, such as monoclonal or polyclonal antibodies, raised against the variant protein (i.e., the protein resulting from the RS2 gene with the aforementioned threonine/isoleucine substitution). Such antibodies may be obtained using standard techniques and may be polyclonal or monoclonal. Polyclonal antibodies can be obtained, for example, by the methods described in Ghose et al. (Methods in Enzymology. Vol. 93:326 327, 1983). An RS2 polypeptide, or an antigenic fragment thereof, is used as an immunogen to stimulate the production of RS2 reactive polyclonal antibodies in the antisera of animals such as rabbits, goats, sheep, rodents and the like. Anti-RS2 antibodies specific for RS2 gene products are raised by immunizing animals with a polypeptide spanning site of the variation (i.e., amino acid 107). Monoclonal antibodies may be obtained by the process described by Milstein and Kohler (1975. Nature. 256:495-497) or as modified by Gerhard (Monoclonal Antibodies. Plenum Press. 1980. pages 370-371). Hybridomas are screened to identify those producing antibodies that are highly specific for the selected RS2 enzyme immunogen.

Antibody binding may also be detected using known methods. For example, an ELISA assay utilizing a substrate (e.g., a plastic dish) coated with antigen comprising a bovine-derived biological sample containing the RS2 gene product. An antibody preparation specific for a known RS2 gene product is added to the well, whereupon the antibody will bind or fail to bind to the sample in the well. Non-binding material is washed away and a marker enzyme (e.g., horse radish peroxidase or alkaline phosphatase, coupled to a second antibody directed against the antigen-specific primary antibody) is added in excess and the nonadherent material is washed away. An enzyme substrate is added to the well and the enzyme catalyzed conversion is monitored as indicative of presence of the variant.

The mutant allele having the SNP encoding an isoleucine at position 107 of the RS2 amino acid sequence may be used as a marker for identifying soybean associated with a low raffinose and stachyose seed content, and a high sucrose seed content. In a preferred embodiment, the mutant allele sequence defined by the single nucleotide polymorphism is used as a marker to select for soybean having this mutant allele for use in breeding programs to produce progeny which will exhibit significantly reduced raffinose and stachyose seed content, and a significantly increased sucrose seed content relative to soybean possessing the wild-type alleles for RS2. Soybean germplasm identified as possessing the mutant allele of this invention would be retained for breeding to incorporate the low raffinose and stachyose seed content, and a high sucrose seed content trait into elite germplasm, such as through backcross breeding. Conversely, soybean germplasm which do not possess the mutant allele would not be selected and would be removed from breeding. Moreover, it is understood that soybean line 397 described herein, or any other line possessing a mutant RS2 allele encoding a threonine to isoleucine change at position 107 of the RS2 amino acid sequence, may be used as breeding parents to produce soybean lines having a low raffinose/stachyose seed phenotype.

The following example is intended only to further illustrate the invention and is not intended to limit the scope of the invention which is defined by the claims.

EXAMPLE 1

Methods and Materials
Population Development

The 'Williams 82' [Bernard & Cremeens: Registration of 'Williams 82' Soybean. *Crop Sci* 1988, 28(6):1027-1028] EMS mutagenized populations screened in this study were described by [Cooper et al.: TILLING to detect induced mutations in soybean. *BMC Plant Biology* 2008, 8(1):9]. The populations screened were exposed to 40 or 50 mM EMS (ethyl-methanesulfonate). $M_1$ plants were advanced to $M_2$ families, leaf tissue was collected and DNA prepared from a single $M_2$ plant from each family. $M_3$ seeds from each $M_2$ plant were catalogued for storage.

Development of RS2 Contrasting Lines

Thirty-nine seeds were planted in packets (CYG, Mega International, St. Paul, Minn.), allowed to germinate, and transferred to soil in flats. Plants were sampled for genotypic determination by allele-specific molecular marker assay described below. A population of only the plants homozygous for either the wild-type or mutant allele of RS2 were transplanted to 3-gallon pots; 1-3 plants per pot. Seven homozygous wild-type and nine homozygous mutant RS2 $M_{2-3}$ plants from the mutagenized line 397 were grown to maturity in a growth chamber with 13 hour day length. The dark temperature was 22° C. and the light temperature was 28° C. Plants were grown, three per 3-gallon pot, in PRO-MIX (Premier Horticulture) medium and fertilized with Osmocote Plus (Scotts) per manufacturer's instructions.

Population Screening
Reverse Genetics Gene Screening

A portion of RS2 was screened for EMS induced mutations. Exon 1 of RS2 was screened using IR 700 and IR 800 labeled primers: 5'-GAGTCTCATATTGTACATGGTAG-3' and 5'-GCAATTCGATGCTTCTTATGAG-3' (SEQ ID NOs: 6 and 7, respectively). Standard TILLING (Targeting induced local lesions in genomes) polymerase chain reaction (PCR) parameters were as follows: One cycle of 95° C. for 2 minutes and 94° C. for 20 seconds followed by 56 cycles of 94° C. for 20 seconds, 56° C. for 30 seconds, and 72° C. for 1 minute. The next step in the PCR was 72° C. for 5 minutes, then a 99° C. step for 10 minutes followed by a 70° C. to 0° C. melt. The reactions were then held at 10° C. Cel I based cleavage of PCR products and detection with polyacrylamide gels was essentially as described [Colbert et al.: High-throughput screening for induced point mutations. *Plant Physiol* 2001, 126(2):480-484].

Pools containing cleaved products indicating an induced mutation or heteroduplex mismatch were deconvoluted by separating the pools into individual plant DNA samples for sequencing in order to identify the line containing the mutation [McCallum et al.: Targeting induced local lesions IN genomes (TILLING) for plant functional genomics. *Plant Physiol* 2000, 123(2):439-442; Colbert et al., ibid; McCallum et al.: Targeted screening for induced mutations. *Nature Biotechnology* 2000, 18:455-457]. The location of the mutation as well as the zygosity could then be verified. The RS2 mutations were confirmed by PCR amplification of a portion of the gene followed by sequence analysis. Primers used were 5'-CCCACCATGTCACCACACC-3' and 5'-GGTGAT-GAATTTTTAGCGGCG-3' (SEQ ID NOs: 8 and 9, respectively). PCR parameters were 95° C. for 10 minutes, followed by 35 cycles of 95° C. for 30 seconds, 60° C. for 30 seconds, and 72° C. for 30 seconds, and then 5 minutes at 72° C.; the reaction was held at 4° C. Screening for the RS2 candidate gene was carried out at Purdue University in West Lafayette, Ind.

Allele-Specific Molecular Marker Assay Development

RS2 Allele-Specific Molecular Marker Assay

An allele specific molecular marker assay was developed for the mutation identified in line 397 to discriminate between wild-type Williams 82 or mutant alleles of the RS2 gene. The assay was designed as described [Wang et al.: High-throughput SNP genotyping by single-tube PCR with Tm-shift primers. *Biotechniques* 2005, 39(6):885-893]. In order to achieve allele specificity, single base pair mismatches were introduced into the primer sequence to increase the discriminatory power of the allele-specific primer. These bases and the tails are indicated in lowercase in the primer sequences. Primer sequences were: 5'-gcgggcGTTGCTACCGACCCAGtGAA-3', 5'-gcgggcagggcggcGTTGCTACCGAC CCAGcGAG-3', and a common forward primer 5'-CAGAGGAATAAAAT-TCATGAGCATA-3' (SEQ ID NOs: 10-12, respectively).

Reactions were carried out in 20 µl; each primer was at 0.5 µM final concentration in reactions containing template, buffer (40 mM Tricine-KOH (pH 8.0), 16 mM KCl, 3.5 mM $MgCl_2$, 3.75 µg $ml^{-1}$ BSA, 200 µM dNTPs), 5% DMSO, 0.25×SYBR Green I, and 0.2× Titanium Taq polymerase (BD Biosciences, Palo Alto, Calif.).

PCR parameters on a DNA Engine Opticon 2 (MJ Research/Bio-Rad, Hercules, Calif.) for the RS2 assay were as follows: 95° C. for 12 minutes followed by 35 cycles of 95° C. for 20 seconds, 60° C. for 30 seconds, 72° C. for 30 seconds, and then a melting curve from 72° C. to 90° C. The fluorescence was read after each cycle and every 0.2° C. with a one second hold during the melt. Each genotype produced a product with a characteristic melting profile, as measured by $T_m$ of the negative first derivative of the disappearance of fluorescent signal. The Williams 82 homozygous genotype gave a peak at 83.6° C., mutant homozygous genotype gave a peak at 79.2° C., and a heterozygous genotype gave a peak at 83.6° C. with a shoulder at 79.0° C. Templates for PCR were 1.2 mm washed FTA (Whatman, Clifton, N.J.) card punches prepared from leaves according to the manufacturer's instructions.

Oligosaccharide Phenotype Determination

Oligosaccharides were determined by high performance ion chromatography with pulsed amperometric detection (PAD) employing an Agilent 1100 series HPLC and an ESA Coulochem III detector (Agilent Technologies, Chesterfield, Mo., USA). A 12.5 mg ground seed sample from either a whole seed or a chipped seed (seed were cut with a razor blade so that approximately ½ could be used for oligosaccharide extract and the remaining half could be germinated) was extracted with 0.5 ml 50% ethanol at 70° C., 30 min. Samples were then centrifuged 15 min at 16,000 g. The supernatant was passed through a 0.2 µm filter. Sugars were separated on a Dionex Carbo Pac PA 10 analytical column (250 mm×4 mm, 10 µm) connected to a Carbo Pac PA 10 guard column (50 mm×4 mm). The mobile phase was 90 mM NaOH with flow rate of 1.5 ml $min^{-1}$, maintained at 30° C. Detection settings were: time 0, 0.1 v, time 0.41, –2.0 v, time 0.42, 0.6 v, and time 0.44, –0.1 v.

Results

Identification of Soybean Raffinose Synthase (RS2) Mutant Alleles

Previously, mutations in the soybean raffinose synthase gene, RS2, have been shown to result in an increase in seed sucrose and a decrease in raffinose and stachyose [Dierking & Bilyeu: Association of a soybean raffinose synthase gene with low raffinose and stachyose seed phenotype. *The Plant Genome* 2008, 1(2):135-145]. Reverse genetics screening of the EMS mutagenized populations created the potential to find additional mutations in RS2 and confirm the contribution of this gene to the seed oligosaccharide phenotype in soybean. A portion of the RS2 gene [GenBank: EU651888] was screened for mutations utilizing the TILLING strategy [Cooper et al., ibid]; four lines were identified which contained single nucleotide polymorphisms (SNPs). These lines were subsequently confirmed by sequence analysis to contain independent RS2 mutations. The four identified lines all contained a SNP typical of EMS mutagenesis, G/C or A/T transitions. Two of the mutations did not result in amino acid changes and therefore were not considered candidates for phenotypic characterization. The other two lines, designated 165 and 397, contained mutations which resulted in missense amino acid changes.

DNA from $M_2$ tissue of line 165 contained a homozygous SNP (c448t in the coding sequence) resulting in S150F amino acid change. DNA from $M_2$ tissue of line 397 contained a heterozygous SNP (c320t in the coding sequence) resulting in a T107I amino acid change. The induced mutations in both line 165 and 397 lie in semi-conserved regions of plant raffinose synthase gene sequences. $M_3$ seedlings from lines 165 and 397 were characterized for the RS2 alleles, and the homozygous and segregating nature of the identified mutant alleles was confirmed, respectively.

Oligosaccharide Content Phenotype of RS2 Induced Mutants

Seeds from the homozygous S150F line 165 did not have an obvious oligosaccharide phenotype as determined by quantitatively measuring sucrose, raffinose and stachyose of $M_3$ seeds and comparing them to wild-type seeds. However, the line 397 harboring the T107I RS2 allele displayed a phenotype predicted for mutations in the soybean raffinose synthase gene RS2.

Taking advantage of the heterozygous state of the induced mutation in line 397, we investigated the inheritance of this novel allele and its subsequent effect on seed oligosaccharide content by screening thirty-seven individual $M_3$ seeds for both oligosaccharide phenotype and RS2 genotype. Seeds were chipped into two approximately equal pieces, one was used for single seed oligosaccharide phenotype analysis and the remaining portion containing the embryo was germinated and genotyped by the developed allele specific molecular marker assay. The genotype/phenotype association results on $M_3$ seeds reveal an increase in sucrose along with decreases in raffinose and stachyose content when seeds were homozygous for the mutant RS2 allele. Furthermore, one wild-type allele of RS2 was sufficient to produce the wild-type oligosaccharide seed phenotype, which is consistent with previous results [Dierking & Bilyeu, ibid].

A population consisting of plants with contrasting RS2 genotypes was then developed from line 397-derived plants that contained either homozygous wild-type (Williams 82) or homozygous mutant alleles at the RS2 locus in order to further characterize the phenotype resulting from the novel allele. Seven independent wild-type RS2 and nine independent mutant RS2 plants were selected to negate the action of unidentified genes that may contribute to the oligosaccharide content. Four seeds from each of the plants of the homozygous population were analyzed for oligosaccharide content. For the plants that contained the T107I RS2 mutation, the average seed sucrose was increased by 28%, raffinose was reduced to 37% and stachyose was reduced to approximately 24% of 397-derived seeds which carried the wild-type allele of RS2. This oligosaccharide phenotype is similar to the phenotype controlled by the previously described RS2 mutant alleles in PI 200508 [[Dierking & Bilyeu, ibid].

In all cases where RS2 was homozygous mutant, a statistically significant difference in the ratio of sucrose to the sum of raffinose and stachyose was observed when compared to seeds with either RS2 homozygous wild-type or heterozygous alleles. The absolute ratios observed in the homozygous classes were significantly different between the segregating seed samples and the homozygous plants analyzed; a higher mean ratio was observed for the field grown seeds compared to the seeds produced in the growth chamber.

Discussion

Multiple variant alleles of the raffinose synthase gene were identified, and one line containing mutant alleles produced the predicted phenotype. The phenotype was confirmed to be dependent on the inheritance of the mutant allele. The developed molecular marker assays enable direct selection for the mutant allele in the heterozygous state, when the phenotype would not otherwise be apparent. Seed mutagenesis and reverse genetics are not transgenic technologies, so soybean varieties that incorporate the mutant alleles are conventional lines which are not subject to any regulatory restrictions. The soybean traits can be rapidly incorporated into elite soybean cultivars and released to producers.

The identification of an induced mutation in RS2 serves as an additional confirmation of the contribution of this gene to the seed raffinose and stachyose content [[Dierking & Bilyeu, ibid]. Similar to the PI 200508 mutant allele of RS2, the mutagenized line 397 has reduced raffinose and stachyose as well as an increase in seed sucrose content. Since similar phenotypes resulted from two independent mutations in RS2, it may indicate that the mutations in the gene are deleterious to enzyme function and the detected raffinose in these lines is the result of one or more additional soybean raffinose synthase genes. It appears that inheritance of a single wild-type allele of RS2 is sufficient for a wild-type oligosaccharide seed phenotype, which is consistent with previously characterized RS2 alleles [[Dierking & Bilyeu, ibid].

Soybean seed oligosaccharide content appears to be controlled mainly by the RS2 gene. However, both raffinose and stachyose are still present in lines containing RS2 mutants, suggesting that additional raffinose synthase enzyme activity remains during seed development. Other candidate raffinose synthase genes have been identified, but variant alleles have not been confirmed to be associated with altered oligosaccharide content. It is possible that combining an RS2 mutation with variant alleles of other raffinose synthases may reveal epistatic interactions that would otherwise have been masked by a wild-type version of RS2.

It is understood that the foregoing detailed description is given merely by way of illustration and that modifications and variations may be made therein without departing from the spirit and scope of the invention.

We claim:

1. A soybean seed, plant or parts thereof comprising a mutant allele of the gene encoding the soybean raffinose synthase 2 enzyme, RS2, which encodes an isoleucine at position 107 of the enzyme amino acid sequence.

2. The soybean seed, plant or parts thereof of claim 1 wherein said amino acid sequence of said soybean raffinose synthase 2 enzyme, RS2, variant comprises SEQ ID NO: 5.

3. The soybean seed, plant or parts thereof of claim 1 wherein said mutant allele comprises SEQ ID NO: 4.

4. The soybean seed, plant or parts thereof of claim 1 which are homozygous for said mutant allele.

5. A method for detecting a mutant allele of the raffinose synthase 2 enzyme, RS2, in soybean, *Glycine max* (L.) Merr., comprising assaying a sample of nucleic acid molecules from a soybean for the presence of a nucleic acid sequence encoding a variant of the soybean raffinose synthase enzyme which comprises an isoleucine at position 107 of the enzyme amino acid sequence.

6. The method of claim 5 wherein said nucleic acid molecules are selected from the group consisting of genomic DNA, cDNA, and RNA.

7. The method of claim 5 wherein said nucleic acid molecules comprise genomic DNA molecules.

8. The method of claim 5 wherein said nucleic acid molecules comprise a DNA molecule that encompasses, or is encompassed by, the soybean raffinose synthase 2 enzyme sequence of SEQ ID NOs: 3 or 4, or a complement thereof.

9. The method of claim 5 further comprising selecting for breeding soybean which comprise said variant.

10. The method of claim 5 further comprising removing those soybean for breeding which do not comprise said variant.

11. The method of claim 5 wherein said variant comprises a single nucleotide polymorphism consisting of an thymine at nucleotide 320 of the coding sequence of said nucleic acid sequence.

12. A method for screening for alleles of the raffinose synthase 2 enzyme, RS2, in soybean, *Glycine max* (L.) Merr., comprising:

a) obtaining a sample of nucleic acid molecules from a soybean b) assaying said sample for the presence of a polymorphism in the raffinose synthase 2 enzyme gene, wherein said polymorphism encodes an isoleucine at position 107 of said raffinose synthase 2 enzyme; and c) selecting for soybean which comprise said polymorphism for breeding.

13. The method of claim 12 further comprising removing from breeding soybean which do not comprise said polymorphism.

14. The method of claim 12 wherein said nucleic acid molecules are selected from the group consisting of genomic DNA, cDNA, and RNA.

15. The method of claim 12 wherein said nucleic acid molecules comprise genomic DNA molecules.

16. The method of claim 12 wherein said nucleic acid molecules comprise a DNA molecule that encompasses, or is encompassed by, the soybean raffinose synthase 2 enzyme sequence of SEQ ID NOs: 3 or 4, or a complement thereof.

17. The method of claim 12 wherein said polymorphism comprises a single nucleotide polymorphism consisting of an thymine at nucleotide 320 of the coding sequence of said raffinose synthase 2 gene.

18. A method for detecting a mutation in the raffinose synthase 2 enzyme, RS2, in soybean, *Glycine max* (L.) Merr., comprising:

a) determining the presence of either an isoleucine or a threonine at amino acid 107 of said raffinose synthase 2 enzyme; and b) selecting for soybean which have said isoleucine at amino acid 107 of said the raffinose synthase 2 enzyme for breeding.

19. The method of claim 18 further comprising removing from breeding soybean which have a threonine at position 107 of said raffinose synthase 2 enzyme.

* * * * *